(12) United States Patent
Beisser et al.

(10) Patent No.: US 10,905,812 B2
(45) Date of Patent: Feb. 2, 2021

(54) HEATING APPARATUS FOR HEATING DIALYSIS LIQUID, DIALYSIS LIQUID TUBE SET, SET, MEDICAL APPARATUS AND METHODS

(71) Applicant: Fresenius Medical Care Deutschland GmbH, Bad Homburg (DE)

(72) Inventors: Nicolas Beisser, Hanau (DE); Stefan Oesterreich, Neu-Ansprach (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 369 days.

(21) Appl. No.: 15/879,656

(22) Filed: Jan. 25, 2018

(65) Prior Publication Data

US 2018/0147337 A1 May 31, 2018

Related U.S. Application Data

(63) Continuation of application No. 13/851,234, filed on Mar. 27, 2013, now Pat. No. 9,913,938.

(60) Provisional application No. 61/616,441, filed on Mar. 28, 2012.

(30) Foreign Application Priority Data

Mar. 28, 2012 (DE) .................. 10 2012 006 149

(51) Int. Cl.
*A61M 1/16* (2006.01)
*A61M 5/44* (2006.01)

(52) U.S. Cl.
CPC .......... *A61M 1/1656* (2013.01); *A61M 1/166* (2014.02); *A61M 1/167* (2014.02); *A61M 5/44* (2013.01); *A61M 5/445* (2013.01); *A61M 2205/14* (2013.01); *A61M 2205/3306* (2013.01); *A61M 2205/6063* (2013.01)

(58) Field of Classification Search
CPC ............ A61J 1/10; A61J 1/12; A61M 1/1656; A61M 1/166; A61M 1/1664; A61M 5/44; A61M 5/445; A61M 2205/14
See application file for complete search history.

(56) References Cited

U.S. PATENT DOCUMENTS

| | | |
|---|---|---|
| 373,764 A | 11/1887 | Demers |
| 2,910,564 A | 10/1959 | McBroom |
| 3,674,970 A | 7/1972 | Bedocs |
| 3,737,604 A | 6/1973 | Dietrich et al. |
| 4,429,202 A | 1/1984 | Tedd |
| 5,335,551 A | 8/1994 | Ohnishi |
| 5,722,947 A | 3/1998 | Jeppsson et al. |
| 5,730,721 A | 3/1998 | Hyatt |
| 6,635,020 B2 | 10/2003 | Tripp, Jr. |

(Continued)

FOREIGN PATENT DOCUMENTS

| | | |
|---|---|---|
| DE | 9403082 | 5/1994 |
| DE | 69530482 | 10/2003 |

(Continued)

*Primary Examiner* — Ibrahime A Abraham
*Assistant Examiner* — John J Norton
(74) *Attorney, Agent, or Firm* — Fish & Richardson P.C.

(57) ABSTRACT

A heating apparatus for heating a dialysis liquid includes a receiving section for receiving a heating bag through which dialysis liquid to be heated can flow, and a sensor system for determining or monitoring the deformation or the position of the heating bag in the receiving section of the heating apparatus or both. A dialysis liquid tube set, a set, a medical apparatus and a method are also described.

11 Claims, 7 Drawing Sheets

(56) References Cited

U.S. PATENT DOCUMENTS

| | | |
|---|---|---|
| 9,248,225 B2 | 2/2016 | Demers |
| 2008/0245785 A1 | 10/2008 | Liang |
| 2009/0009179 A1 | 1/2009 | Sobue et al. |
| 2009/0299273 A1 | 12/2009 | Lee et al. |
| 2009/0312694 A1 | 12/2009 | Bedingfield et al. |
| 2010/0021148 A1 | 1/2010 | Theilacker-Beck |
| 2011/0198289 A1 | 8/2011 | Jonsson |
| 2012/0031826 A1 | 2/2012 | Childers et al. |

FOREIGN PATENT DOCUMENTS

| | | |
|---|---|---|
| DE | 102010036295 | 3/2012 |
| DE | 102010055781 | 6/2012 |
| EP | 2468390 | 6/2012 |
| WO | WO 2009/106354 | 9/2009 |
| WO | WO 2010/025824 | 3/2010 |

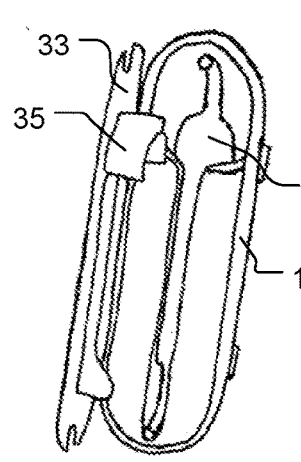
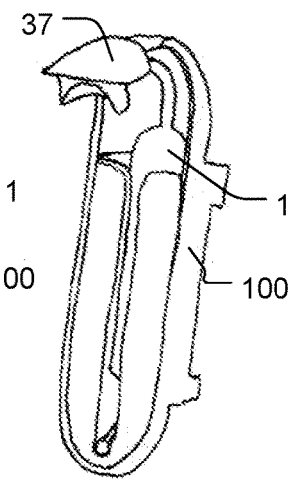
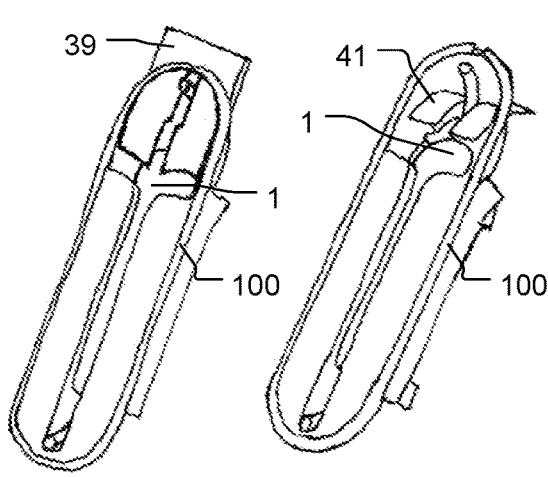
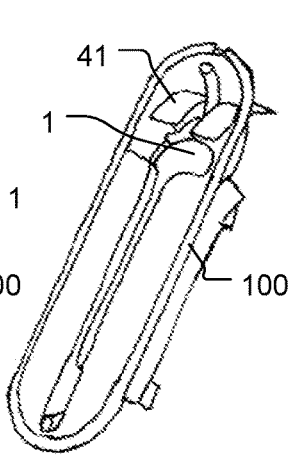
Fig. 6a  Fig. 6b  Fig. 6c  Fig. 6d
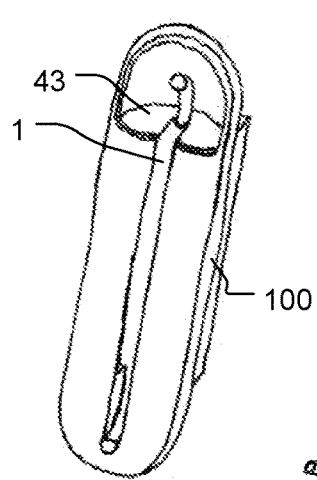
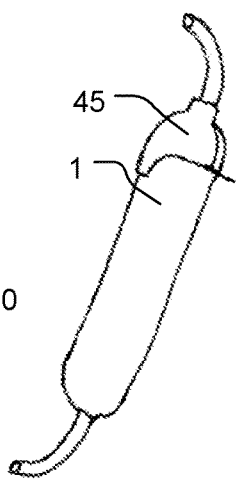
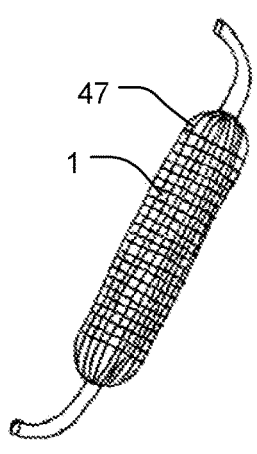
Fig. 6e  Fig. 6f  Fig. 6g

HEATING APPARATUS FOR HEATING DIALYSIS LIQUID, DIALYSIS LIQUID TUBE SET, SET, MEDICAL APPARATUS AND METHODS

CROSS REFERENCE TO RELATED APPLICATIONS

This application is a continuation application of and claims priority under 35 U.S.C. § 120 to U.S. patent application Ser. No. 13/851,234, filed on Mar. 27, 2013, which claims priority to U.S. Provisional Application Ser. No. 61/616,441, filed on Mar. 28, 2012, and Application No. DE 10 2012 006 149.8, filed in the Federal Republic of Germany on Mar. 28, 2012. Each application is expressly incorporated herein in its entirety by reference thereto.

FIELD OF INVENTION

The present invention relates to a heating apparatus. It further relates to a dialysis liquid tube set, a set, a medical apparatus, and a method.

BACKGROUND INFORMATION

International Patent Publication No. WO 2010/025824 A2 describes apparatuses by means of which dialysis liquid is heated by means of a heating bag during a dialysis treatment. Heating takes place while the dialysis liquid flows through the heating bag, before the dialysis liquid is introduced into the dialyzer or blood treatment filter, in which substances are exchanged between blood and dialysis liquid via a—usually semipermeable—membrane.

Under certain operating conditions, it can however not be excluded, without having taken countermeasures, that the heating bag bursts due to the pressure built up by the pump which conveys the dialysis liquid through the heating bag. Bursting could take place especially in arrangements in which the heating bag is arranged on the pressure side of the pump—for example to avoid precipitations in the tube system. Bursting of the heating bag may pose a danger to the patient, at least if it is not noticed in time.

SUMMARY

An object of the present invention is to propose apparatuses and methods to decrease the risk that a heating bag bursts during the dialysis treatment or bursts unnoticed.

Thus, according to the present invention, a heating apparatus is proposed for heating a dialysis liquid which is present in a heating bag. The dialysis liquid flows during use through the heating bag for being heated, or it can flow through it. The heating apparatus comprises a receiving section for receiving the heating bag. Further, the heating apparatus comprises a sensor system. The sensor system is at least one of arranged, provided, designed, configured or programmed for determining or monitoring a deformation or longitudinal expansion of the heating bag or the location or position of the heating bag which it occupies within the heating apparatus or within the receiving section of the heating apparatus, or both.

Further, according to the present invention, a dialysis liquid tube set is proposed. The dialysis liquid tube set is provided or designed to be inserted into the heating apparatus according to the present invention.

According to the present invention, a set is furthermore proposed. The set according to the present invention comprises a heating apparatus according to the present invention with at least one receiving section for receiving a heating bag. Further, the set comprises at least one dialysis liquid tube set, which—being preferably integral herewith—comprises at least one heating bag through which the dialysis liquid can flow.

The dialysis liquid tube set or the receiving section of the set—or both—are chosen, determined or coordinated such that the length of the heating bag is always less than the length of the receiving section of the heating apparatus. This way, it is ensured that the receiving section radially delimits or at least could delimit the heating bag, which is inserted herein, during its use along its entire length. This means that the heating bag or sections hereof cannot leave the interior of the receiving section even if the heating bag expands—and possibly expands till it bursts.

Further, according to the present invention, a medical apparatus is proposed which comprises at least one heating apparatus according to the present invention or is connected therewith.

In addition, a method for heating dialysis liquid within a dialysis liquid tube set is proposed. The dialysis liquid tube set comprises a flow-through heating bag for the dialysis liquid to be heated. The method encompasses inserting the heating bag in a receiving section of a heating apparatus of a medical apparatus. The method further encompasses selecting—in advance—the utilized dialysis liquid tube set and/or the flow-through heating bag which is present therein. The heating bag and the receiving section are thereby coordinated or matched such that the length of the heating bag along which the receiving section surrounds the heating bag when it is inserted in the receiving section and/or filled with dialysis liquid is always smaller or less than the length of the receiving section.

In all of the following exemplary embodiments, the use of the expression "may be" or "may have," and so on, is to be understood synonymously with "preferably is" or "preferably has," respectively, and so on, and is intended to illustrate an exemplary embodiment according to the present invention.

Exemplary embodiments according to the present invention may comprise one or more of the features and advantageous developments described hereafter.

In certain exemplary embodiments of the present invention, the receiving section is designed to allow a deformation of the heating bag, which is received herein, in only one extension direction, due to an interior pressure of the heating bag.

As an extension direction, in certain exemplary embodiments of the present invention, the longitudinal axis of the heating bag or of the receiving section is understood, wherein an extension is allowed in these exemplary embodiments in both of the opposite directions of a straight line which is determined by the longitudinal axis. In other exemplary embodiments of the present invention, an extension is permitted in only one of the two opposite directions of the straight line.

The sensor system is in certain exemplary embodiments of the present invention a purely mechanically acting or functioning apparatus, or both, which does not comprise electronic elements. In other exemplary embodiments of the present invention, the sensor system is a purely electronically acting or functioning apparatus, or both. In some exemplary embodiments according to the present invention, the sensor system comprises at least one of mechanically, electronically or optically acting or functioning elements.

In certain exemplary embodiments of the present invention, the sensor system for monitoring the deformation of the heating bag comprises or consists of at least one mechanical, one optical sensor, one element which is mounted to be movable, a press key, or arbitrary combinations of the before-mentioned elements.

In some exemplary embodiments of the present invention, the sensor system is designed, arranged or both designed and arranged for determining the longitudinal expansion of the heating bag, preferably of a front end of the heating bag, in particular its head section.

In some exemplary embodiments according to the present invention, the sensor system is neither a weighing device nor comprises such. Weighing devices may, for example, work according to the principle that a weight, e.g., that of a heating bag, or the change of its weight, is measured with a bending beam and strain gages which reflect or detect the deflection of the bending beam or another change.

In certain exemplary embodiments according to the present invention, the receiving section is designed such that it encloses the heating bag in a circumferential direction hereof—or in a plane perpendicular to the flow direction of the dialysis liquid within the heating bag or to the longitudinal axis of the heating bag—during its use. Thereby, the heating bag is enclosed along its whole length.

"Enclosing" means in some exemplary embodiments of the present invention that the receiving section surrounds the heating bag during its use along the whole circumference of the heating bag or lies flat against it or contacts it. Alternatively, the receiving section surrounds the heating bag not along the whole circumference, but only to an extent of at least 70%, 80%, 90% or 95%, or the receiving section surrounds the heating bag in radial direction at least such that the heating bag can be extracted from the receiving section only along its longitudinal direction, but not in its transverse direction. The latter applies to the heating bag in a filled condition or in an empty condition or independent of the filling condition of the heating bag.

In some exemplary embodiments of the present invention, the heating apparatus is designed to enclose the flow-through heating bag in each operating condition cylindrically, sleeve-like or pipe-shaped or lie flat against the heating bag in this way. In doing so, the before-mentioned definition of "enclosing" can apply.

The receiving section is in some exemplary embodiments of the present invention designed to withstand an inside/internal pressure of the heating bag of 1050 mbar over a period of 72 hours. Further, it has to withstand 10 loading conditions over a period of each 20 seconds with a pressure of each 3200 mbar in these exemplary embodiments and is designed accordingly.

For receiving the pressures which occur when the heating bag is being filled, the wall or limitation of the receiving section is in some exemplary embodiments of the present invention accordingly designed. For example, a longitudinal slot of the receiving section, through which the drain line of the heating bag can be led or fed through when the heating bag is being inserted (see FIG. 5a), is limited to a value of a range from 5 mm to 15 mm width, preferably to a value of a range from 8 mm to 10 mm, e.g., 8 mm. This design allows the receiving section to withstand the internal pressure. The actually freely selectable dimension of the opening of the housing of the heating apparatus may be slightly narrower or less than the gap dimension of the cylindrical wall described below.

In some exemplary embodiments according to the present invention, the heating apparatus or the receiving section comprises at least one reinforcing element which is arranged to effect reinforcement of the receiving section against radially acting pressure from the heating bag. Thus, for example, a cylindrical wall of the receiving section may be provided at an exterior of the receiving section in radial direction with one or more, e.g., 2, 3, 4 or more, reinforcing elements such as steel clips or clamps.

In addition or as an alternative to the reinforcing elements mentioned before, for reinforcement against mechanical stress by the heating bag the wall of the receiving section is in some exemplary embodiments of the present invention made of ceramics, or it comprises ceramics.

In some exemplary embodiments of the present invention, the sensor system of the heating apparatus comprises a sensor which is suitable and used for detecting or recording a longitudinal extension.

In certain exemplary embodiments of the present invention, the sensor of the sensor system determines or reports the location of the heating bag relative to a receiving level or state of the heating bag before its longitudinal extension. For example, the sensor may determine or report a later extension of the heating bag based on the later location, position or extension of the heating bag compared to the bag's previous location, position or extension.

In certain exemplary embodiments of the present invention, the sensor system comprises an element which is provided or mounted to be movable. The element is, for example, designed as a mechanical tactile sensor, and hereafter it is denoted as such in a simplifying but non-restrictive way. By means of the mechanical tactile sensor, a detected longitudinal extension is signalized in certain exemplary embodiments according to the present invention in that the mechanical tactile sensor, preferably in a mechanical or another way, actuates a switch or an apparatus such as a micro switch. The actuation of this switch or this apparatus directly or indirectly leads to the consequences of the alarm as described herein, such as a stopping of the pump, a slowdown of the pump or other suitable measures.

In some of these exemplary embodiments according to the present invention, the heating apparatus further comprises an additional checking apparatus which is arranged for testing, when being actuated, the correct function of the sensor system, the movably mounted element such as for example the mechanical tactile sensor, the switch and/or the apparatus singularly or in arbitrary combinations. For example, the checking apparatus is in some exemplary embodiments of the present invention designed as a mechanical or hydraulic element which is arranged for actuating the switch, for example the micro switch, like the mechanical tactile sensor, but independent hereof, or it comprises such an element. By actuating the checking apparatus, it is possible to test the function of the switch.

In some exemplary embodiments of the present invention, the checking apparatus is arranged to act on the mechanical tactile sensor or to move it such that it actuates the switch on his part. With the checking apparatus being arranged this way, it is possible to check both the function or movability of the mechanical tactile sensor and the function of the switch when the checking apparatus is being actuated for test reasons.

A performance test for the switch—with or without testing the mechanical tactile sensor at the same time—can take place automatically and, for example, every time the heating apparatus is being started.

The checking apparatus may comprise or consist of a lifting magnet or solenoid and a rotating element. The solenoid is advantageously suitable to be actuated in a contact-free way also from an exterior of the heating apparatus. The rotating element allows to act on the mechanical tactile sensor in a space-saving way, by means of the solenoid, or in a different way.

In some exemplary embodiments of the present invention, the rotating element transfers a linear movement of a first element, e.g., a bar, a solenoid or a ram or piston, to a second linear element. The rotating element and the two linear elements can be in one level. The rotating element can be arranged on an axis or shaft to be rotatable, for example on a pin on which the rotating element is mounted to be rotatable (e.g., by means of a slide bearing).

The second linear element can be the tactile pin. The rotating element can engage in or with the tactile pin to move it when the rotating element rotates.

In some exemplary embodiments of the present invention, the rotating element is designed to be able to move the tactile pin during a rotation (in that the rotating element for example contacts a stop of the tactile pin), without being moved itself if the tactile pin is moved by another element than the rotating element.

In some exemplary embodiments of the present invention, the deformation or longitudinal expansion of the heating bag in axial direction is a measure for the material stress of the heating bag or it is—in particular completely or essentially completely—a result of it. Monitoring the longitudinal expansion of the heating bag can allow a conclusion on the material stress in the moment of monitoring. The material stress can be compared with values that were previously recorded. If admissible limit values for material stress, which are mostly recorded or saved, are reached or exceeded, an alarm can be output or the operation of an apparatus, for example the pump, by means of which the heating bag is filled, can be stopped or slowed down.

In some exemplary embodiments of the present invention, the heating apparatus comprises an apparatus for outputting an alarm or an apparatus for stopping or slowing down a pump which conveys the dialysis liquid through the heating bag, or both. Thereby, the apparatuses are configured, set up or programmed for outputting an alarm or for stopping the pump, if or when the sensor system detects a predetermined deformation of the heating bag, a predetermined location of the heating bag in the receiving section, a predetermined material stress or arbitrary combinations hereof.

In certain exemplary embodiments of the present invention, a dialysis liquid tube set or system is inserted into the heating apparatus. The dialysis liquid tube set comprises—preferably manufactured integrally with the tube set—at least one heating bag. The heating bag is provided for herein heating dialysis liquid from the dialysis liquid tube set by the heating apparatus.

The explanations made herein with respect to the dialysis liquid apply in certain exemplary embodiments of the present invention also to substituate. Also, the explanations made here with regard to dialysis liquid tube sets apply in certain exemplary embodiments of the present invention also to substituate tube sets.

In some exemplary embodiments according to the present invention, the dialysis liquid tube system is designed as a one-way product or disposable.

In some exemplary embodiments according to the present invention, the dialysis liquid tube system is a dialysis liquid tube.

In some exemplary embodiments of the present invention, the medical apparatus comprises an apparatus for monitoring a correct arrangement of the heating bag in the receiving section, or for monitoring that the longitudinal expansion of the heating bag does not exceed a predefined limit value, or both. The medical apparatus further comprises an apparatus for outputting an alarm or an apparatus for stopping or slowing down a pump which conveys the dialysis liquid through the heating bag, or both.

In certain exemplary embodiments of the present invention of the medical apparatus, it is designed as a blood purification device, for example as a dialysis apparatus, as a filtration apparatus, as a diafiltration apparatus, or as a dialysis apparatus in any other exemplary embodiment for blood purification which is known to the person skilled in the art.

The medical apparatus is in certain exemplary embodiments according to the present invention configured for use for the continuous venous hemodiafiltration (CVV-HDF) and/or configured for use for acute dialysis.

In certain exemplary embodiments according to the present invention, the medical apparatus according to the present invention is connected with an extracorporeal blood circuit and/or a tube system.

In certain exemplary embodiments of the present invention, it encompasses inserting the heating bag such that a front end of the heating bag rests on or is in contact with a bottom section of the receiving section when being inserted or due to inserting. This way, it is ensured that the heating bag can expand or extend only in one direction along its longitudinal direction, namely away from the bottom section, but not towards it.

A heating bag is in some exemplary embodiments of the present invention the section of a dialysis liquid tube set, which by being filled is dilated according to its intended use or can be filled under its radial expansion.

A heating bag is in certain exemplary embodiments of the present invention the section of a dialysis liquid tube set which has a thinner wall thickness than adjacent tube sections.

A "flow-through" heating bag is in some exemplary embodiments of the present invention a heating bag which comprises an inlet and at least one supply line which is connected herewith. The heating bag further comprises a drain which is separate from at least one drain line which is connected herewith. Thereby, the supply line or the drain line, or both, each have a diameter which does not correspond to a maximum diameter of the heating bag during use.

In some exemplary embodiments of the present invention, the extension direction or expansion direction of the heating bag is the direction in which the flow streams during use. In certain exemplary embodiments, this is the direction of its longitudinal axis or longitudinal extension. Wherever herein a direction or axis is mentioned, an expansion in one direction or in both (opposite) directions along the extension or axis can be meant.

The length of the heating bag is in some exemplary embodiments of the present invention understood to be a longitudinal extension of the heating bag, which it can assume during use. In certain exemplary embodiments of the present invention, the length is understood to be the longitudinal extension of the heating bag which the heating bag can assume as a maximum before it bursts if its radial expansion is prevented or limited in that the whole heating bag radially contacts or lies flat or could contact or lie flat against the receiving section.

The length of the receiving section of the heating apparatus is in certain exemplary embodiments of the present invention understood as the dimension of the receiving section in its longitudinal direction while—preferably completely or essentially—the cross-section or inner circumference of the receiving section along which the heating bag contacts or could contact does not change even if or when it expands due to increasing internal pressure in the bag.

"Determining" or "monitoring" as used herein can be or encompass checking or detecting whether a sensor recognizes the presence of a section of the heating bag at a predetermined spot of the receiving section or the heating apparatus.

In some exemplary embodiments according to the present invention, "determining" or "monitoring" as used herein means not solely determining, monitoring or checking whether a heating bag is inserted into a receiving section or a heating apparatus. "Solely" can be understood herein as a digital condition. It is determined, monitored or checked, for example, whether a heating bag is inserted into a receiving section or a heating apparatus at all ('Yes') or is not inserted ('No'). In these exemplary embodiments, "determining" or "monitoring" also means or encompasses identifying where the heating bag or a section thereof is present.

In certain exemplary embodiments according to the present invention, "determining" or "monitoring" as used herein means determining, monitoring or checking whether a heating bag has been inserted into a receiving section or a heating apparatus at all, or not (for example its presence is verifiable at a certain location or position), but not at which location or position inside of the heating apparatus the heating bag is present.

"Determining" or "monitoring" may take place metrologically, and the sensor system can be accordingly designed.

In some exemplary embodiments according to the present invention, the heating apparatus comprises at least one fixation device for fixing the lower tube section (or a section thereof) at the heating apparatus and/or for restraining device for assuring that the lower end of the bag in its intended or predetermined use is arranged at the lower end of the heating apparatus and/or remains there.

For example, the heating apparatus can have, e.g., at its front side, a clamping device into which a section of the lower tube section, which is guided to an outside through the slot of the front side, is clamped—or fixed in any other way than clamping. For creating a form closure and/or a traction or force closure between the lower tube section and the heating apparatus, e.g., the front side thereof, can be provided.

To this end, the vertical or longitudinal slot can, in a preferred exemplary embodiment according to the present invention, be lead (e.g., for a short distance) upwardly ascending in a U shaped manner at its lower end, for example by a multiple of the diameter of the tube of the lower tube section. Hereby the lower tube section can be upwardly redirected once the heating bag has been correctly inserted. The clamping device can thereby optionally advantageously act as strain relief, by which the redirected tube section can be securely set or fixed.

Additionally or alternatively, the lower tube section can comprise a restraining element (e.g., a plastic sleeve, e.g., with at least one ledge or edge at or around its circumference). The restraining device allows for a form locking setting or arrangement of the lower tube section on the heating apparatus (e.g., at the slot, at the clamping device, if provided, etc.). The clamping device, if provided, can hereby act as abutment and absorb the tensile or tractive forces acting on the tube.

Alternatively or additionally, in some exemplary embodiments according to the present invention, a frictional fixation or restraining or force closure is achieved or provided by a half-open (half-pipe) or longitudinally slotted, trough shaped tube guiding element into which the lower tube section is pushed under elastic deformation and is, thereby, frictionally set or fixed.

Some or all exemplary embodiments according to the present invention may provide for one, several or all of the advantages named above and/or hereafter.

An advantage according to the present invention is that a bursting of the heating bag due to high internal pressure can be prevented since it is supported by the receiving section along its whole length radially or in circumferential direction—and even after expansion of the heating bag. An expansion of the heating bag is thus at most possible in its longitudinal direction. A local overstress and uneven stress of the heating bag is thus prevented.

Another advantage which is achievable by means of the present invention is that by the sensor system a control can take place whether the heating bag was correctly inserted. Further, it can be monitored by the sensor system that the heating bag cannot expand or extend beyond a predefined degree unnoticed. As such expansion would be recognized by the sensor system, required measures can be taken in time.

Yet another advantage of the present invention may be that the functionality of the sensor system can be checked by the checking apparatus in a simple and reliable way. This may take place separately or together for the mechanical tactile sensor and the switch or a corresponding apparatus.

The checking apparatus may hereby be provided in constricted or limited space. It may be actuated touchlessly from outside the heating apparatus.

In some exemplary embodiments according to the present invention, an advantage can be found in that during use the heating bag is inserted into the heating apparatus reliably completely down to its end or stop. Moreover, in certain exemplary embodiments according to the present invention, after the correct insertion of the heating bag, the heating bag cannot accidentally be pulled out during the further set up of the tube set at the medical apparatus such that the lower end of the bag is no longer set at the lower end of the heating apparatus. This can also be advantageously prevented by exemplary embodiments according to present invention.

Exemplary embodiments of the present invention are hereafter described with reference to the appended drawings, in which identical reference numerals refer to same or similar components.

BRIEF DESCRIPTION OF THE DRAWINGS

FIGS. 6a to 6g show in a schematically simplified way variants for receiving the heating bag in the heating apparatus according to the present invention in a pressure-resistant way.

DETAILED DESCRIPTION

Figure 1:
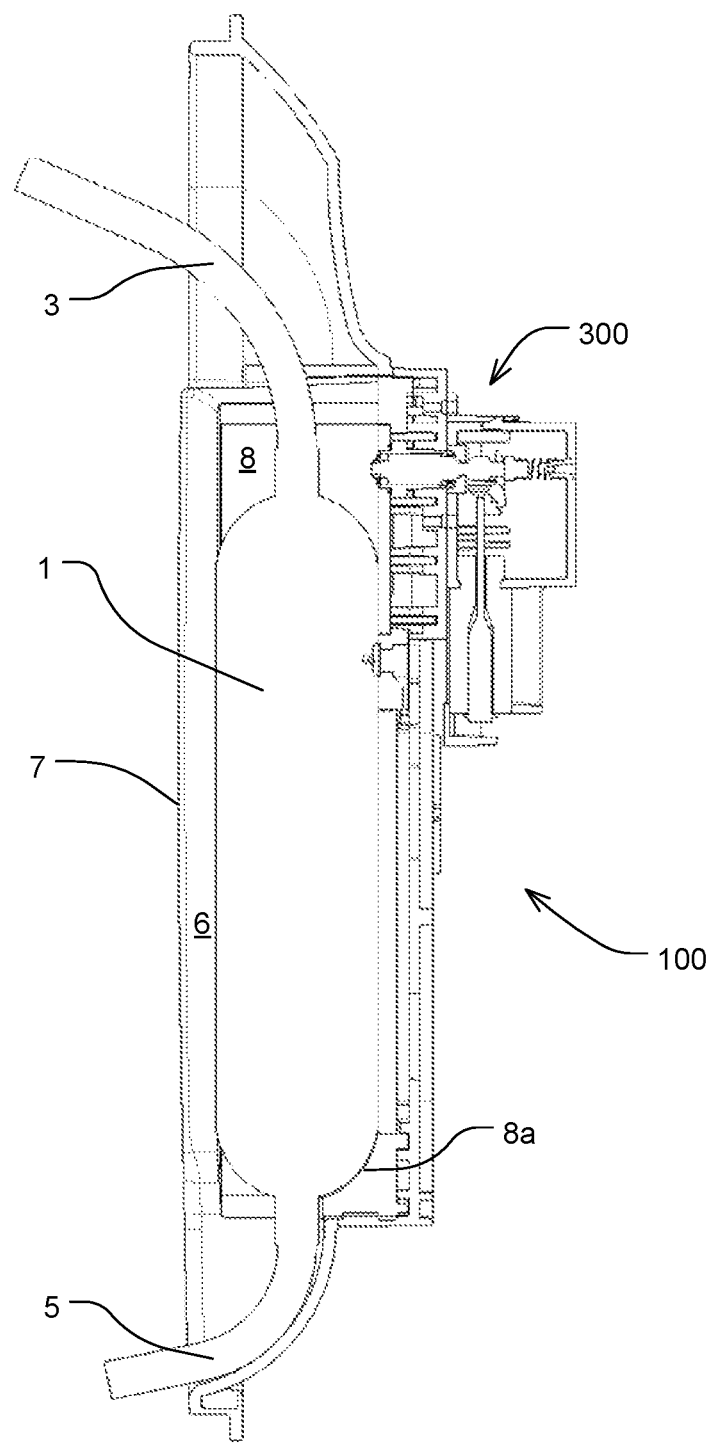
FIG. 1 schematically shows in a section view a heating apparatus according to the present invention with a heating bag and a sensor system for detecting the heating bag.

FIG. 1 schematically shows in a section view a heating apparatus 100 according to the present invention with an inserted heating bag 1. The heating bag 1 comprises an upper tube section 3 as supply line and a lower tube section 5 as drain line (or vice versa), which can be connected or which is connected with a tube set 700, 800 (see FIG. 7).

Figure 2:
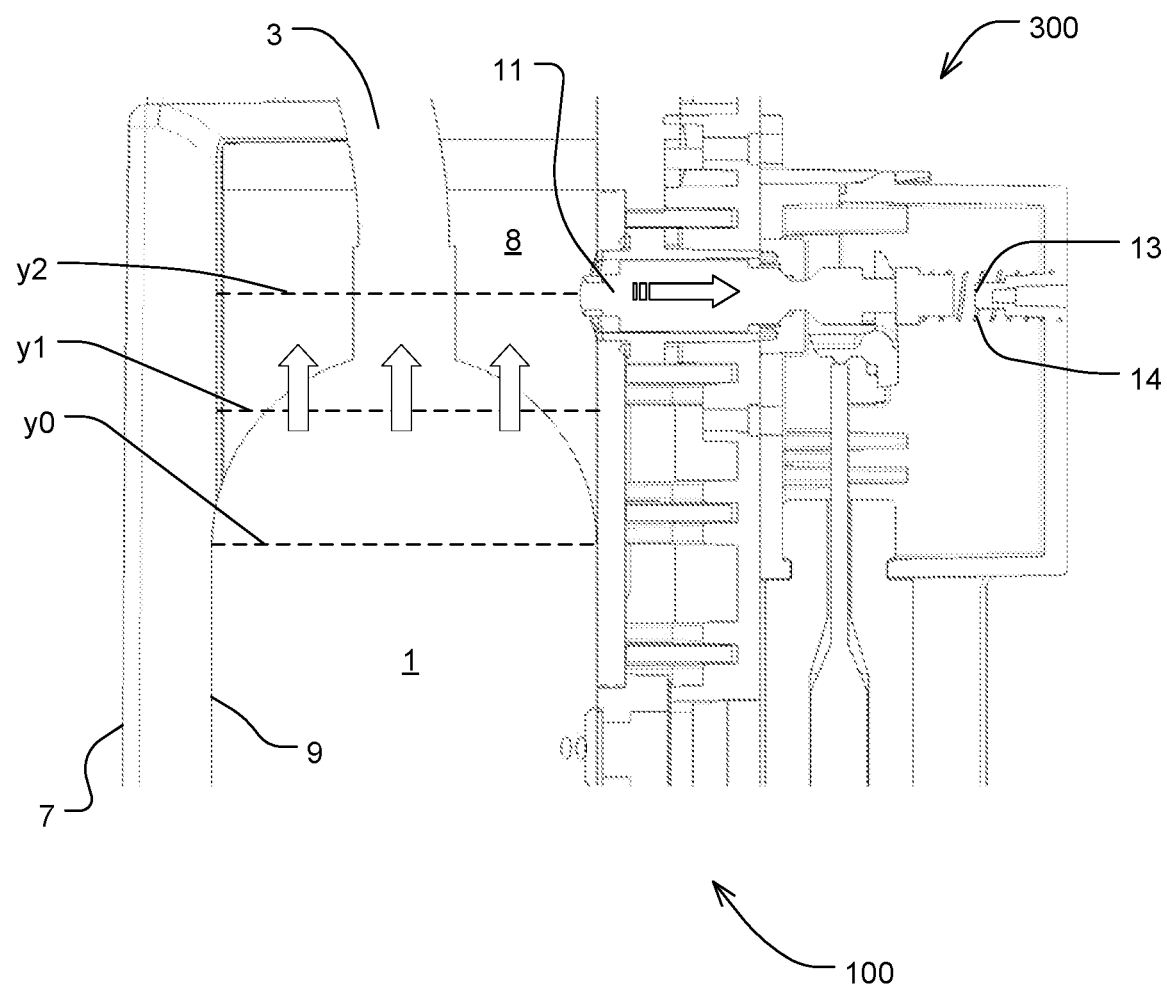
FIG. 2 shows a detail of the heating apparatus according to the present invention from FIG. 1.

Furthermore, the heating apparatus 100 comprises a sensor system 300 adapted for detecting an expansion of the heating bag 1, e.g., caused by an increased fluid internal pressure, in longitudinal direction (see also FIG. 2 for the sensor system 300).

The heating bag 1 is almost completely enclosed by the heating apparatus 100 in radial circumferential direction. Only a longitudinal slot 6 remains as an opening on the front side 7 of the heating apparatus 100. Through the longitudinal slot 6, the lower tube section 5 can be pushed through into a receiving section 8 which is located behind the longitudinal slot 6, in order to be able to readily introduce or insert the heating bag 1 into the heating apparatus top-down. The longitudinal slot 6 is embodied according to FIGS. 6a to 6e.

If the dialysis liquid flows through the heating bag 1, either through the upper tube section 3 as fluid inlet or supply line and the lower tube section 5 as fluid outlet or drain line, or vice versa, the dialysis liquid is heated in a controlled manner by the heating apparatus 100.

In the illustration of FIG. 1, the heating bag 1 can only expand upwards (related to FIG. 1) and thus in its longitudinal extension, as the heating bag 1 is limited by the wall of the receiving section 8 in radial or in circumferential direction along its whole length and beyond. In addition, the heating bag 1 is limited with its lower face end or foot by a bottom section 8a. The bottom section 8a is recognizable in FIG. 1 as domed. It is thus recreated to the shape of the heating bag 1 in its filled condition or copies the same. Any other shape of the bottom section 8a is however also encompassed by the present invention.

The present invention comprises in some exemplary embodiments a restraining device, which is not shown in the figures, for assuring that the lower end of the bag, during its intended or predetermined use, is set at the lower end of the heating apparatus and/or remains there.

By way of example, the lower end of the heating bag 1 may be set at the lower end of the heating apparatus 100, by setting or fixing the lower tube section 5, which is guided out of the slot 6 from the front side of the heating apparatus 100, at or to the front side 7 of the heating apparatus 100 by form closure and/or traction, in a defined or predetermined manner. To this end, in a preferred exemplary embodiment, the vertical slot 6 can be guided or lead (e.g., by a short distance) upwardly, ascending in a U-shaped manner at its lower end, for example by a multiple of the diameter of the lower tube section 5. Hereby the lower tube section 5 can be upwardly redirected once the heating bag 1 has been correctly inserted, wherein a clamping device provided, e.g., at the front side 7 of the heating apparatus 100, can act as strain relief, by which the redirected tube section 5 can be securely set or fixed at the front side 7 of the heating apparatus 100.

Additionally or alternatively, the lower tube section 7 can comprise a restraining or fixation element which is not shown in the figures (e.g., a plastic sleeve, e.g., with at least one ledge or edge, arranged on or around its circumference) which allows for a form locking setting of the lower tube section onto the clamping device, wherein the clamping device can hereby act as an abutment and absorb the tensile or tractive forces acting on the tube.

Alternatively or additionally, in some exemplary embodiments according to the present invention, a frictional fixation or restrainment is provided by means of a half-open or longitudinal slotted, trough shaped tube routing or guiding element, into which the lower tube section 5 is pushed under elastic deflection and thereby is frictionally set or fixed.

FIG. 2 shows a detail of FIG. 1 with a sensor system 300 to detect the heating bag 1 or its location within the receiving section 8.

In the initial position, the heating bag 1 in the receiving section 8 is in position y0. There is no overpressure in the heating bag 1. The position y0 is where the heating bag 1 just barely still has contact with the inner side 9 of the receiving section 8. If the fluid pressure rises, the heating bag 1 expands. This expansion and its direction is indicated in FIG. 2 by three parallel arrows. A rising fluid pressure can be caused by an increased fluid resistance downstream from the heating apparatus 100, for example by an increased filter resistance, or by an increased fluid pressure upstream. Due to the increasing fluid pressure, the heating bag 1 expands for example such that it still has contact with the inner side 9 up to position y1. If the fluid pressure increases even further, the heating bag 1 has contact with the inner side 9 up to position y2 or possibly even higher.

At position y2, the sensor system 300 of the heating apparatus 100 according to the present invention comprises a sensor which in this exemplary embodiment is an element in the form of a tactile pin 11, which is arranged to be mechanically movable, and a micro switch (tactile pin 11 with micro switch are also denoted as mechanical tactile sensor). Once the expansion of the heating bag 1 has reached the position y2, and if the heating bag 1 in the position y2 still has contact with the inner side 9, the heating bag 1 moves the tactile pin 11 in the direction of the horizontal arrow. Consequently, the micro switch (not described in more detail here) is activated, which can for example output an electric signal.

The tactile pin 11 can be completely moved (or pressed) to a stop 13. The stop can prevent a tilting of the tactile pin 11. Further, a spring 14 for pre-stressing or returning the tactile pin 11 can be provided.

The micro switch may output a signal, which in turn can trigger an alarm in a connected processing and/or control unit for reporting a fault. By the alarm, suitable countermeasures can be initiated. For example, the pump filling the heating bag can be stopped or slowed down in order to prevent a bursting of the heating bag 1 due to continuing pump performance.

The alarm indicates that a predetermined limit value of a longitudinal expansion or of a limit position of the heating bag 1 has been reached and/or exceeded. The limit value is in this case exceeded at position y2. In the exemplary embodiment shown here, position y2 is 20 mm away from position y0, and position y1 is 10 mm away from position y0. The limit value y2 thus indicates a maximum admissible deformation of the heating bag 1, before measures are taken or at least an alarm takes place.

The sensor system 300 can furthermore be used for controlling the location of the heating bag 1. For example, an incorrectly inserted heating bag can be detected as the sensor system 300 is activated by the heating bag 1 already before the heating bag 1 has been filled or before the dialysis treatment has been started.

Figure 3A:
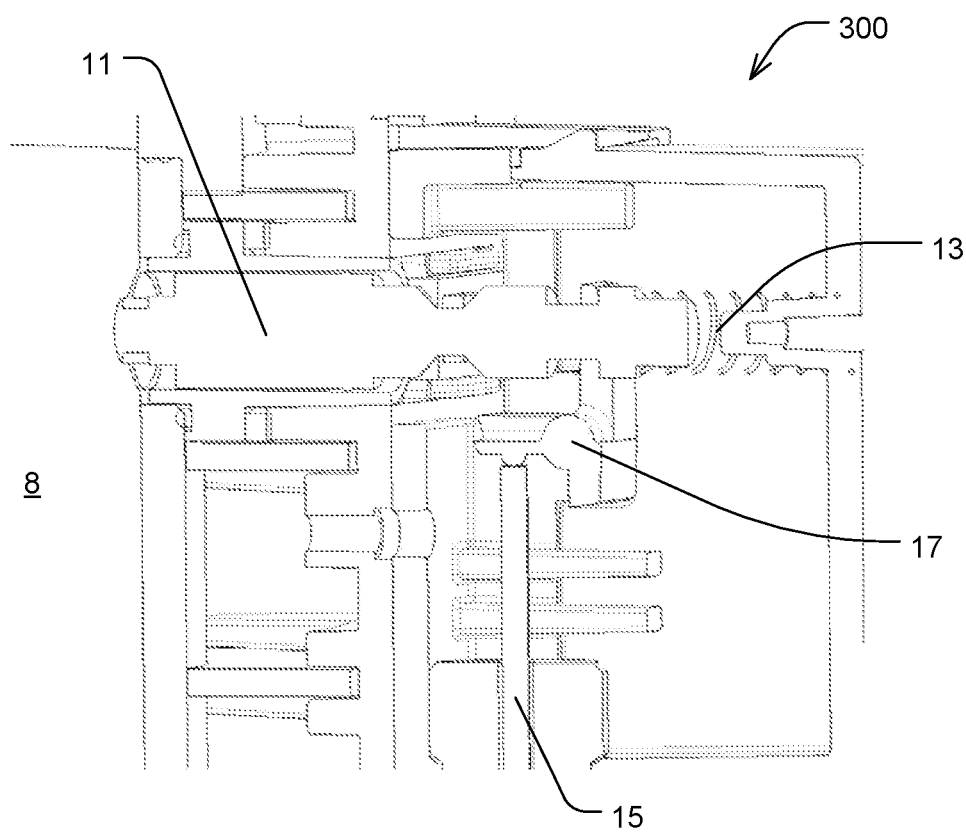
FIGS. 3a and 3b schematically show the sensor system from FIG. 2 in a non-activated or an activated test position.
Figure 3B:
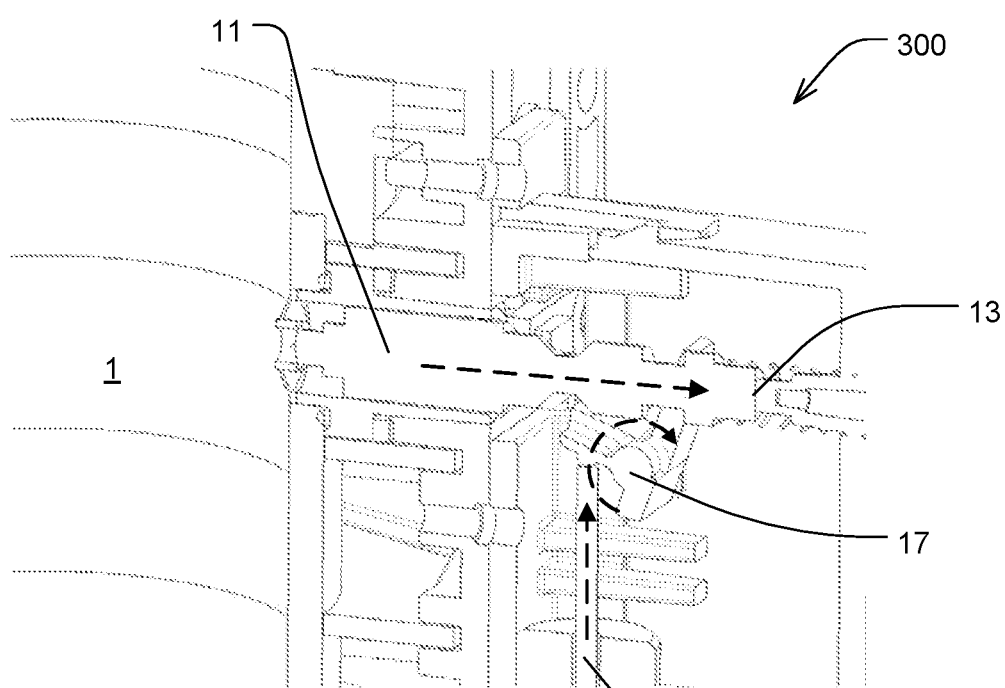

FIGS. 3a and 3b schematically show the sensor system 300 from FIG. 2 in a non-activated (FIG. 3a) or an activated (FIG. 3b) test position.

Before the heating apparatus 100 is being used, the sensor system 300 can be tested with respect to its function (so-called "self-test"). This is in particular relevant if the tactile pin 11 with the micro switch is a safety-relevant protective device of an overall system. Thereby, if possible, not only the micro switch should be checked, but also the activation of the micro switch by the tactile pin 11. A manual actuation of the tactile pin 11 by the user is not considered to be useful and may moreover be forgotten. Hereinafter, a mechanism for such a test is described, which can also be performed automatically.

For the self-test, a checking apparatus is provided. In the example of the Figures, it comprises a solenoid 15 and a rotating element 17. In exemplary embodiments other than the one shown here, it is sufficient to provide only a magnet but not also a rotating element. The magnet would then pull the tactile pin 11 towards the micro switch.

In the illustration of FIG. 3 however, the solenoid 15, which is controlled or activated from outside, controls the tactile pin 11 via a rotating element 17. The tactile pin 11 is then moved, limited by the stop 13. In doing so, the micro switch is actuated through the tactile pin 11 and triggers a signal, as described above.

In FIG. 3b, the movements of the tactile pin 11, the solenoid 15 and the rotating element 17 during the functional test are indicated by means of three broken lines. The linear movement directions of the tactile pin 11 and the solenoid 1 are in an angle to each other which here is, for example, 90°. The transfer of the movement of the solenoid 15 to the tactile pin 11 thereby takes place by the rotating element 17. The angle which is thus possible between the movements of the two elements 11 and 15, which does not have to be 90° but can also be larger or smaller than 90°, allows for a space-saving arrangement of the checking apparatus. It can, for example as shown here, be parallel to the longitudinal extension of the receiving section 8 and be arranged to be closely mounted or arranged to it.

FIGS. 3a and 3b readily show, especially when being compared with each other, that during its rotation the rotating element 17 drives the tactile pin 11. The rotating element 17 is, however, designed such that the tactile pin 11 can be moved independently from a rotation of the rotating element 17.

Figure 4:
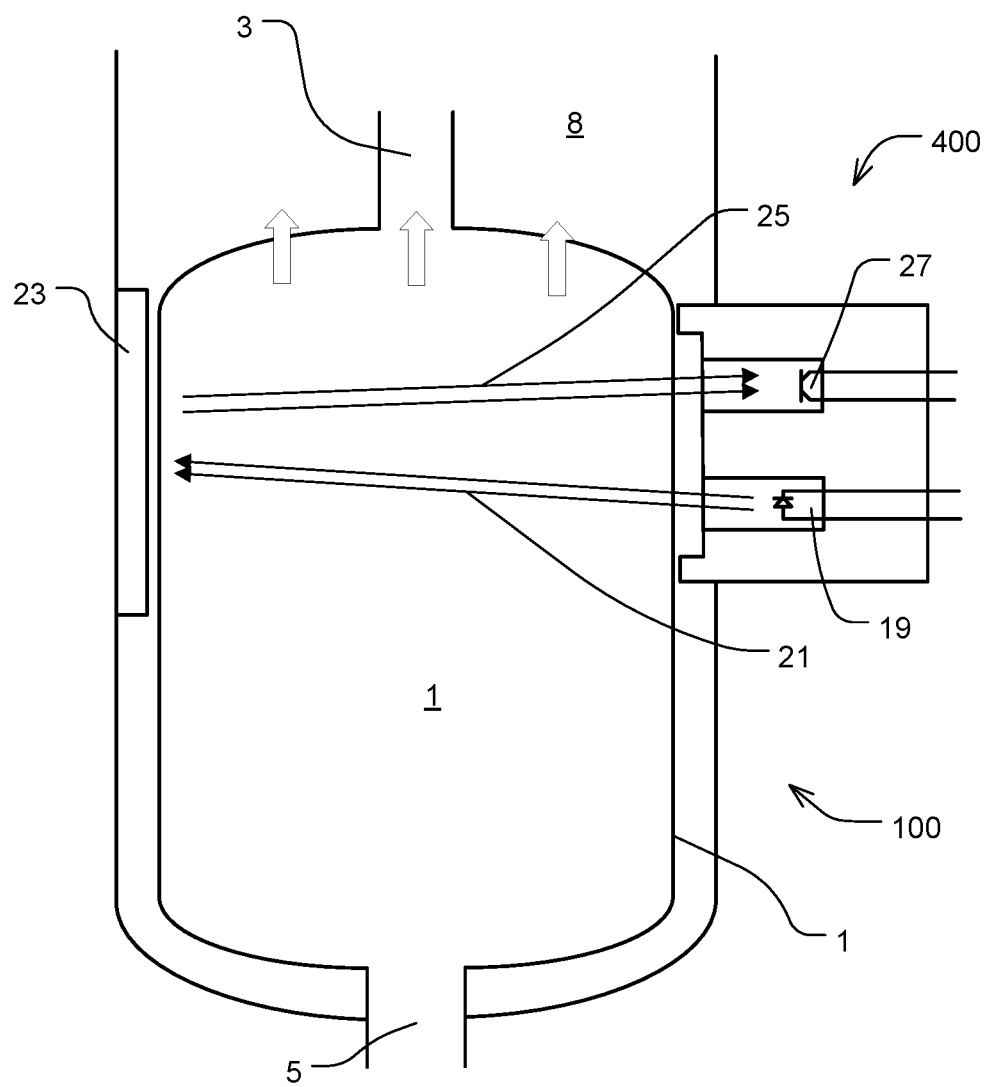
FIG. 4 schematically shows the principle of a light barrier for detecting the heating bag according to the present invention.

FIG. 4 shows in a schematically simplified way a reflected light barrier 400 for detecting the heating bag 1 in a heating apparatus 100.

The reflected light barrier 400 can be used as an alternative (or in addition as a further safety device) to the sensor system 300 shown in FIGS. 1 to 3 with tactile pin 11 and micro switch for detecting the heating bag 1. The reflected light barrier 400 may be used at the same position of the receiving section 8 as the sensor system 300.

With the aid of the reflected light barrier 400, both an initially incorrectly inserted heating bag 1 and a heating bag 1 which is expanded too much can be detected—as with the exemplary embodiment shown in FIGS. 2 and 3.

Furthermore, it is, analogous to the function tests described in FIG. 3, possible before use of the heating apparatus 100 to check the reflected light barrier 400 initially before use. In this initial test, the sensitivity of the reflected light barrier 400 is set to its maximum value with the aid of a switch and a software program (neither of which is described or shown here). For example, the range of the light barrier (maximum distance of a detected object) may be at least 33 mm, in order to bridge an interior space of a cylinder of the heating apparatus 100. The light 21 emitted by a light source, for example an infrared (IR) diode 19, is analyzed and evaluated at the opposite side of the cylinder. Alternatively, it is reflected at a reflector 23, as shown in FIG. 4. If the light 25 reflected by the reflector 23 can be reabsorbed by the reflected light barrier 400 with the aid of a suitable apparatus such as for example a photodiode 27 (or a phototransistor), and a corresponding voltage signal can be read by the photodiode 27, the functional test is considered to be passed, and the reflected light barrier 400 can be used to detect the heating bag 1 in the heating apparatus 100. This mode for testing in which a maximum value of the sensitivity or range is set or pre-set, is denoted herein as test mode for the light barrier.

If a heating bag 1 is inserted in the heating apparatus 100, the sensitivity or the range of the reflected light barrier 400 is being reduced by means of the software program. In this case, the light 21 emitted by the IR diode 19 should detect neither the opposite reflector 23 nor the tube section 3 or the tube section 5 but exclusively the wall of the heating bag 1. The range of the reflected light barrier 400 could be set to, for example, about 5 mm for this purpose.

With the such reduced range, the heating bag 1 is not detected during failure-free operation, i.e., without increased fluid pressure, because it is below the reflected light barrier 300 (with respect to FIG. 4). The tube section 3 or the tube section 5 is also not detected as it is above ("above" relates to the figures and stands for the direction in general in which the heating bag is allowed to expand within the heating apparatus 100 according to the present invention) the decreased range, for example about 15 mm away from the reflected light barrier 300. The outer wall of the heating bag 1 could however be detected by the reflected light barrier 300 if the fluid pressure of the heating bag 1 is increased and the heating bag 1 is therefore expanded thus at the level of the reflected light barrier 300.

This applies both to an initially incorrectly inserted heating bag 1 and to a heating bag 1 which expanded during its use due to an increased fluid pressure and/or an increased temperature of the fluid. This mode, in which a small sensitivity or range for detecting the heating bag 1 is set, is denoted as operating mode or treatment mode of the light barrier.

The operating mode can also be used to initially identify if a heating bag 1 of a previous use or treatment is still inserted. This test could be performed directly after the actual initial test (test mode).

FIGS. 5a to 5d schematically show a cylindrical wall 29 of the receiving section 8 of the heating apparatus 100 with different numbers of reinforcing elements 31.

Figure 5A:
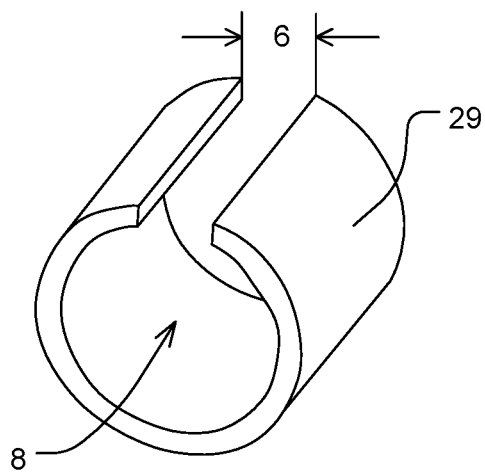
FIGS. 5a to 5d schematically show a cylindrical wall of the heating apparatus, partially with reinforcing elements.

The cylindrical wall 29 may be a pipe with a radial slot 6 in longitudinal direction, as illustrated in FIG. 5a.

The cylindrical wall 29, hereafter denoted as wall 29, is an integral part of the heating apparatus 100. The wall 29 can be integrated into the housing of the heating apparatus 100, for example a plastic or resin housing. The wall 29 surrounds the receiving section 8 and in this way essentially the heating bag 1 which is inserted in the heating apparatus 100. The wall 29 prevents expansion of the heating bag 1 in radial direction, in particular under fluid overpressure in the heating bag 1. Depending on the stiffness of the wall 29, the wall allows only or mainly an expansion of the heating bag 1 in its longitudinal direction (see FIG. 1: the expansion of the heating bag 1 takes place upwards in longitudinal direction).

The material of the wall 29 may be or comprise ceramics, e.g., Rubalit. The material may be or comprise a synthetic material (e.g., polyvinyl chloride (PVC)), or it may be a different material.

The reinforcing elements 31, if provided, serve for reinforcing the wall 29, in particular for increasing the stiffness of the wall 29. In particular with a synthetic wall 29, the at least one reinforcing element 31 can increase the stiffness notably.

Figure 5B:
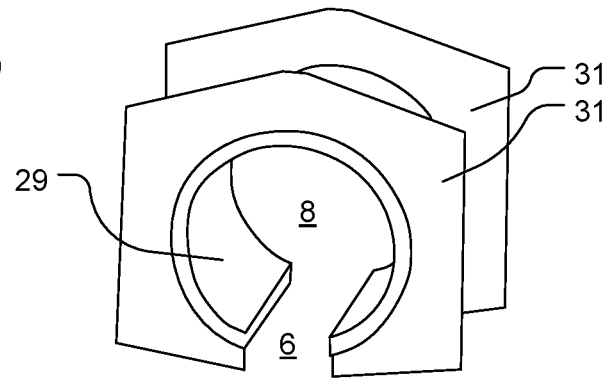
Figure 5C:
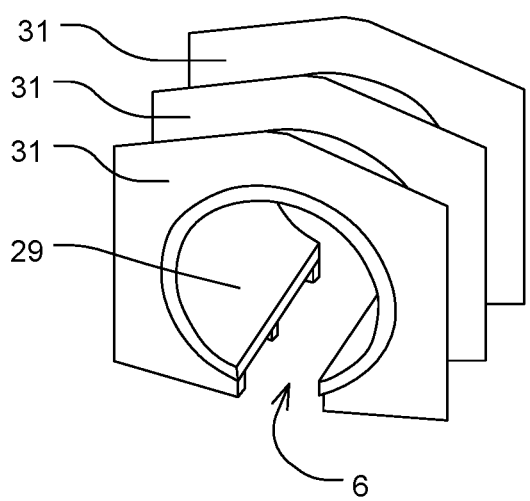
Figure 5D:
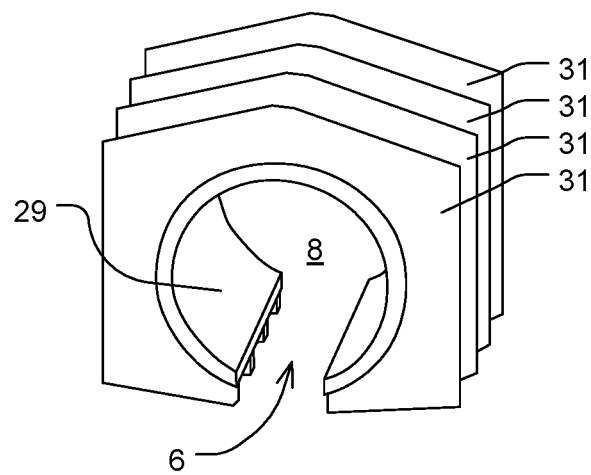

The arrangement and the number of reinforcing elements 31 around the wall 29 may differ. In FIGS. 5b and 5d, exemplary arrangements and numbers of reinforcing elements 31 are shown without being understood to limit the present invention thereto. In FIG. 5b, the wall is provided with two reinforcing elements 31, in FIG. 5c with three reinforcing elements 31, and in FIG. 5d with four reinforcing elements 31. More or less reinforcing elements than shown here may also be provided according to the present invention. The reinforcing elements 31 may be made of metal, for example steel, or of a different material.

The reinforcing elements 31 may be between 1 mm and 5 mm thick, for example 2 mm.

The reinforcing elements may be rib-shaped. In particular, they may be arranged with a main extension direction which is perpendicular to the longitudinal direction of the receiving section.

The cylindrical wall 29 of the receiving section 8 of the heating apparatus 100 may be designed as a separate element, but it may also be designed to be integral with the heating apparatus 100. The cylindrical wall 29 may for example be designed as a sleeve, in particular as a retrofittable sleeve.

FIGS. 6a to 6g show in a schematically simplified view different variants for pressure-resistant reception of the heating bag 1 in the heating apparatus 100.

In FIG. 6a, the heating bag 1 is fixed in the heating apparatus 100 by a side door 33 and a cover 35 which is integrated in this door for the upper part of the heating bag 1. Under increased fluid pressure inside the heating bag 1, an expansion of the heating bag 1 in radial direction of the heating bag 1 is prevented or at least restricted by means of this fixation.

In FIG. 6b, the heating bag 1 is fixed in the heating apparatus 100 by a flap 37 which is turned down from above.

In FIG. 6c, the heating bag 1 is fixed in the heating apparatus 100 by a slide 39 which is movable in the longitudinal direction of the heating apparatus 100.

In FIG. 6d, the heating bag 1 is fixed in the heating apparatus 100 by a pivoting slide 41 or a rotary slide.

In FIG. 6e, the heating bag 1 is fixed in the heating apparatus 100 by a cover 43.

In FIG. 6f, the heating bag 1 is fixed in the heating apparatus 100 (not illustrated here) by a clip 45 which is mounted or arranged at the heating bag 1.

In FIG. 6g, the heating bag 1 is fixed in the heating apparatus 100 (not illustrated here) by means of a net 47 which is put around the heating bag 1.

Figure 7:
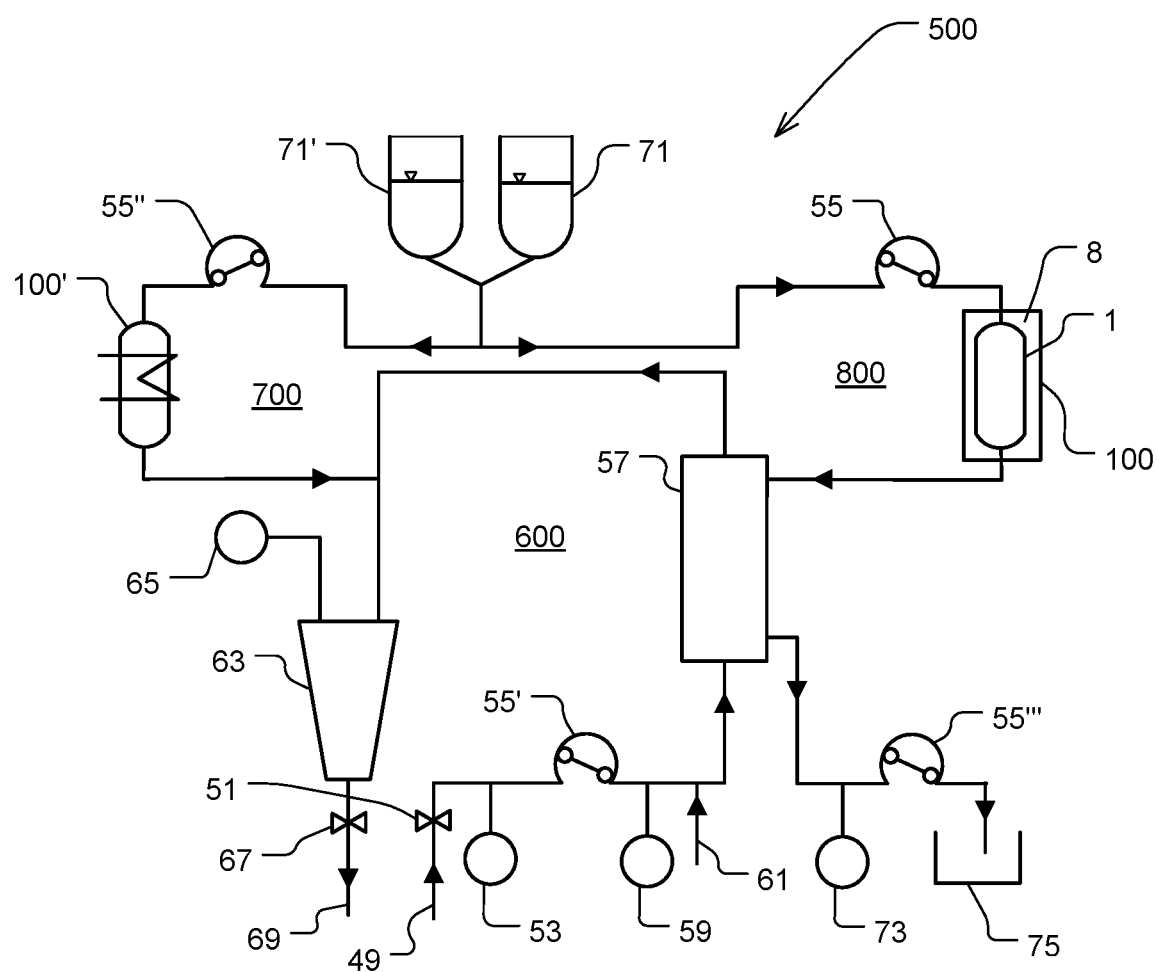
FIG. 7 schematically shows a medical apparatus according to the present invention for dialysis, with an extracorporeal blood circuit, a heating apparatus according to the present invention and a dialysis liquid tube set.

FIG. 7 schematically shows a medical apparatus 500 according to the present invention (also denoted as treatment system) for dialysis, with an extracorporeal blood circuit 600, a substituate tube set 700 and a dialysis liquid tube set 800.

By an arterial connector 49 of an arterial line of the extracorporeal blood circuit 600, blood is taken from the patient. Downstream from the arterial connector 49, a shut-off valve 51 is optionally arranged. Further downstream herefrom, the arterial pressure is optionally measured by means of a pressure sensor 53, and even farther downstream, a blood pump 55' is arranged. Between the blood pump 55' and the connector of the arterial line to the dialyzer 57, the hemofiltration pressure is optionally measured by a pressure sensor 59. Downstream from this pressure sensor 59, heparin is optionally added to the blood for anticoagulation purposes at an addition point 61.

In the dialyzer 57, the exchange of substances takes place with the dialysis liquid of the dialysis liquid tube set 800, which leaves the dialyzer 57 as dialysate. This is explained in more detail farther below.

Downstream from the dialyzer 57, the blood flows into an optionally provided venous drip chamber 63 in which the venous pressure is measured by means of an optionally provided pressure sensor 65. Downstream herefrom, a shut-off valve 67 is optionally arranged. The blood is returned into the vascular system of the patient by a venous connector 69.

The substituate tube set 700 serves to substitute to the patient a part of the liquid volume which was extracted from the blood by the filtration in the dialyzer 57 during the treatment. For this, substituate liquid is taken from a bag 71 or 71', from which also the dialysis liquid may be sourced or provided. The substituate is conveyed in the substituate tube set 700 by means of a substituate pump 55" into a heating apparatus 100' and heated there, and subsequently added to the blood circuit 600.

The dialysis liquid tube set 800, which may be provided as a one-way tube system ("disposable"), is filled with a dialysis liquid from a bag 71. The dialysis liquid is conveyed in the dialysis liquid tube set 800 by a pump 55 which is here only exemplarily designed as a roller pump. In doing so, the dialysis liquid from the bag 71 can flow between the bag 71 and the heating apparatus 1 which is located downstream from the pump 55, i.e., on the pressure side of the pump 55, by gravity and/or by suction of the pump 55. In the heating bag 1, the dialysis liquid is heated by the heating apparatus 100 according to the present invention.

Due to the fluid pressure which is built up by the pump 55, a pressure of approx. 50 mbar may arise in the tube system downstream from the pump 55 during the treatment of the patient. This pressure may increase to 1050 mbar during a treatment. If the flow is blocked through the tube system located downstream, for example due to a corresponding condition of the filter, a maximum pressure of 3200 mbar can be reached.

Farther downstream from the pump 55 and downstream from the heating apparatus 1, the dialyzer 57 is arranged. Downstream from the dialyzer 57, the filtrate pressure is optionally measured by a pressure sensor 73, farther downstream, the dialysate is conveyed into a collection container 75 together with the filtrate by a pump 55''', or it is discarded.

What is claimed is:

1. A heating apparatus for heating a dialysis or substituate liquid, the heating apparatus comprising:
    a receiving section for receiving a heating bag through which the dialysis or substituate liquid can flow for being heated, the receiving section configured for allowing the deformation of the heating bag due to an interior pressure of the heating bag in only one extension direction of the heating bag;
    a sensor system for determining or monitoring a deformation of the heating bag or a location of the heating bag along the receiving section of the heating apparatus, the sensor system comprising:
        a tactile pin positioned along an upper portion of the receiving section, the tactile pin arranged to be contacted by the heating bag as the heating bag deforms along the upper portion of the receiving section; and a switch; and a checking apparatus that is arranged and operative for automatically performing a self-test of the sensor system, wherein an activation of the checking apparatus causes the tactile pin to activate the switch and thereby trigger a signal from the switch that indicates the sensor system is functional.

2. The heating apparatus according to claim 1, wherein the heating apparatus or the receiving section comprises at least one reinforcing element which is arranged for effecting a reinforcement of the receiving section against a radially acting pressure of the heating bag.

3. The heating apparatus according to claim 1, wherein the heating apparatus is configured for enclosing the flow-through heating bag with respect to a circumferential direction of the heating bag along a whole length of the heating bag, and wherein the whole length of the heating bag is less than a length of the receiving section.

4. The heating apparatus according to claim 1, wherein the receiving section is arranged for cylindrically enclosing the heating bag.

5. The heating apparatus according to claim 1, wherein the sensor system for monitoring the deformation the heating bag comprises at least one mechanical or one optical sensor.

6. The heating apparatus according to claim 1, further comprising:

an apparatus for outputting an alarm or for stopping a pump which conveys the dialysis or substitute liquid through the heating bag, wherein the apparatus is configured for outputting the alarm or for stopping the pump if or when the sensor system determines the heating bag is at a limit position along an upper portion of the receiving section.

7. The heating apparatus according to claim 1, further comprising:

a dialysis or substitute liquid tube set configured to be inserted in the heating apparatus and comprising the heating bag configured for heating the dialysis or substituate liquid in conjunction with the heating apparatus.

8. The heating apparatus according to claim 1, wherein the checking apparatus comprises a solenoid arranged to activate the sensor system.

9. The heating apparatus according to claim 1, wherein the checking apparatus comprises a magnet arranged to activate the sensor system.

10. The heating apparatus according to claim 1, wherein the checking apparatus comprises a solenoid, and wherein the activation of the checking apparatus causes the solenoid to move the tactile pin to activate the switch and thereby trigger the signal from the switch that indicates the sensor system is functional.

11. A set, comprising:

the heating apparatus according to claim 1, which comprises the receiving section for the heating bag; and at least one dialysis liquid tube set configured to be inserted in the heating apparatus, wherein the dialysis liquid tube set comprises the heating bag, and wherein a length of the heating bag is less than a length of the receiving section of the heating apparatus.

* * * * *